United States Patent
Hallett et al.

(10) Patent No.: US 6,914,065 B2
(45) Date of Patent: Jul. 5, 2005

(54) IMIDAZO[1,2-C]PYRIMIDINE DERIVATIVES AS LIGANDS FOR GABA RECEPTORS

(75) Inventors: David James Hallett, Watford (GB); Michael Geoffrey Neil Russell, Welwyn Garden City (GB); Leslie Joseph Street, little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 27 days.

(21) Appl. No.: 10/416,242
(22) PCT Filed: Nov. 8, 2001
(86) PCT No.: PCT/GB01/04997
§ 371 (c)(1),
(2), (4) Date: May 7, 2003
(87) PCT Pub. No.: WO02/38569
PCT Pub. Date: May 16, 2002

(65) Prior Publication Data
US 2004/0138236 A1 Jul. 15, 2004

(30) Foreign Application Priority Data
Nov. 10, 2000 (GB) ............................................. 0027561

(51) Int. Cl.⁷ .................... C07D 487/04; A61K 31/519; A61P 25/22; A61P 25/24
(52) U.S. Cl. ..................................... 514/259.1; 544/281
(58) Field of Search ........................ 514/259.1; 544/281

(56) References Cited

U.S. PATENT DOCUMENTS 6,013,799 A 1/2000 Hutchison et al.

FOREIGN PATENT DOCUMENTS

WO    WO 99 19323 A    4/1999

OTHER PUBLICATIONS

Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, pp. 451 and 596.*
Tully W. R. et al: "General Approach Leading to the Development of Imidazoquinoline Andimidazopyrimidine Benzodiazepine Receptor Ligands" Drug Development Research, vol. 22, 1991, p. 299–308.
Krogsgaard–Larsent et al: Gaba Receptor Agonists, Partial Agonists, and Antagonists. Design and Therapeutic Prospects: Journal of Medicinal Chemistry, American Chemical Society, Washington, US, vol. 37, No. 16, Ausut 5, 1994, p. 2489–2505.

* cited by examiner

Primary Examiner—Thomas C. McKenzie
(74) Attorney, Agent, or Firm—J. Eric Thies; Melvin Winokur

(57) ABSTRACT

A class of 3-phenylimidazo[1,2-c]pyrimidine derivatives, of the formula I:

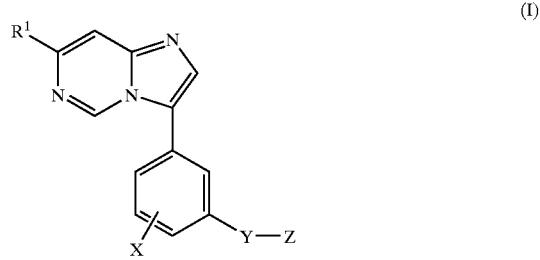

(wherein $R^1$, X, Y, and Z are defined herein) are selective ligands for GABA-A receptors and are useful in the treatment or prevention of adverse conditions of the central nervous system, including anxiety and convulsions.

8 Claims, No Drawings

IMIDAZO[1,2-C]PYRIMIDINE DERIVATIVES AS LIGANDS FOR GABA RECEPTORS

CROSS REFERENCE TO RELATED APPLICATIONS

This application is a U.S. National Phase application under 35 U.S.C. §371 of PCT Application No. PCT/GB01/04997, filed Nov. 8, 2001, which claims priority under 35 U.S.C. § 119 from GB Application No. 0027561.0, filed Nov. 10, 2000.

The present invention relates to a class of substituted imidazo-pyrimidine derivatives and to their use in therapy. More particularly, this invention is concerned with imidazo [1,2-c]pyrimidine analogues which are substituted in the 3-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha1\beta2\gamma2$, $\alpha2\beta\gamma1$, $\alpha2\beta2/3\gamma2$, $\alpha3\beta\gamma2/3$, $\alpha4\beta\delta$, $\alpha5\beta3\gamma2/3$, $\alpha6\beta\gamma2$ and $\alpha6\beta\delta$. Subtype assemblies containing an $\alpha1$ subunit are present in most areas of the brain and are thought to account for over 40% of $GABA_A$ receptors in the rat. Subtype assemblies containing $\alpha2$ and $\alpha3$ subunits respectively are thought to account for about 25% and 17% of $GABA_A$ receptors in the rat. Subtype assemblies containing an $\alpha5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha1$ subunit in combination with a $\beta$ subunit and $\gamma2$. This is the most abundant $GABA_A$ receptor subtype, and is believed to represent almost half of all $GABA_A$ receptors in the brain.

Two other major populations are the $\alpha2\beta\gamma2$ and $\alpha3\beta\gamma2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha5$-containing subtype assemblies. The physiological role of these subtypes has hitherto been unclear because no sufficiently selective agonists or antagonists were known.

It is now believed that agents acting as BZ agonists at $\alpha1\beta\gamma2$, $\alpha2\beta\gamma2$ or $\alpha3\beta\gamma2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha1$ subunit. Accordingly, it is considered that $GABA_A$ receptor agonists which interact more favourably with the $\alpha2$ and/or $\alpha3$ subunit than with $\alpha1$ will be effective in the treatment of anxiety with a reduced propensity to cause sedation. Also, agents which are antagonists or inverse agonists at $\alpha1$ might be employed to reverse sedation or hypnosis caused by $\alpha1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may also be effective as premedication prior to anaesthesia or minor procedures such as endoscopy, including gastric endoscopy.

In addition, the compounds in accordance with the present invention may be useful as radioligands in assays capable of detecting compounds capable of binding to the human GABA$_A$ receptor.

The present invention provides a class of imidazopyrimidine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity (K$_i$) for the α2 and/or α3 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

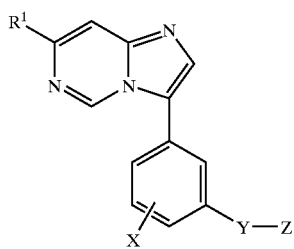

(I)

wherein

X represents hydrogen or halogen;

Y represents a chemical bond, an oxygen atom, or a —NH— linkage;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and R$^a$ and R$^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, amino, formyl, C$_{2-6}$ alkoxycarbolnyl, —CR$^a$=NOR$^b$, trifluoromethyl, C$_{1-6}$ alkoxy and —CONR$^a$R$^b$.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of C$_{3-7}$ cycloalkyl(C$_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl(C$_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyraziliylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In one embodiment, X represents hydrogen.

In another embodiment, X represents halogen, especially fluorine.

In a preferred embodiment, Y represents a chemical bond.

In another embodiment, Y represents an oxygen atom.

In a further embodiment, Y represents a —NH— linkage.

Representative values for the substituent Z include phenyl, pyridinyl, thienyl and thiazolyl, any of which groups may be optionally substituted. In a favoured embodiment, Z represents an optionally substituted phenyl group, in particular monosubstituted phenyl.

Examples of typical substituents on the group Z include chloro, methoxy, trifluoromethyl, cyano, nitro, amino, formyl, methoxycarbonyl and —CH=NOH, especially cyano. Additionally, Z may be substituted by fluoro.

Specific values of Z include trifluoromethylphenyl, cyanophenyl, nitrophenyl, methoxyphenyl, pyridinyl, (amino)(chloro)pyridinyl, cyano-thienyl, formyl-thienyl, methoxycarbonyl-thienyl, thienyl-CH=NOH and thiazolyl. Additionally, Z may represent (cyano)(fluoro)phenyl or difluoropyridinyl.

A particular value of Z is cyanophenyl, especially 2-cyanophenyl.

Suitably, $R^1$ represents hydrocarbon, a heterocyclic group, halogen, trifluoromethyl, —$OR^a$, —$COR^a$, —$CO_2R^a$ or —$CR^a$=$NOR^b$.

Typical values of $R^a$ include hydrogen and $C_{1-6}$ alkyl. Suitably, $R^a$ represents hydrogen or methyl.

Typical values of $R^b$ include hydrogen, $C_{1-6}$ alkyl, hydroxy($C_{1-6}$)alkyl and di($C_{1-6}$)alkylamino($C_{1-6}$)alkyl. Suitably, $R^b$ represents hydrogen, methyl, ethyl, hydroxyethyl or dimethylaminoethyl. Particular values of $R^b$ include hydrogen, hydroxyethyl and dimethylaminoethyl.

Illustrative values of $R^1$ include $C_{1-6}$ alkyl, halo($C_{1-6}$)alkyl, dihalo($C_{1-6}$)alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl and —$CR^a$=$NOR^b$, in which $R^a$ and $R^b$ are as defined above.

Specific values of $R^1$ include methyl, hydroxymethyl, hydroxyethyl, furyl, chloro, fluoromethyl, difluoromethyl, trifluoromethyl, methoxy, formyl, acetyl, methoxycarbonyl and —$CR^2$=$NOR^3$, in which $R^2$ represents hydrogen or methyl, and $R^3$ represents hydrogen, hydroxyethyl or dimethylaminoethyl. Additionally, $R^1$ may represent hydroxypropyl.

Particular values of $R^1$ include methyl, fluoromethyl, difluoromethyl, trifluoromethyl and hydroxymethyl. In one embodiment, $R^1$ represents methyl. In another embodiment, $R^1$ represents trifluoromethyl.

A particular sub-class of compounds according to the invention is represented by the compounds of formula IIA, and salts and prodrugs thereof:

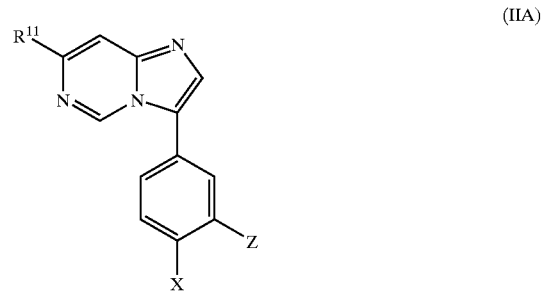

(IIA)

wherein

X and Z are as defined above;

$R^{11}$ represents $C_{1-6}$ alkyl, halo($C_{1-6}$)alkyl, dihalo($C_{1-6}$)alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl or —$CR^4$=$NOR^5$;

$R^4$ represents hydrogen or $C_{1-6}$ alkyl; and $R^5$ represents hydrogen, $C_{1-6}$ alkyl, hydroxy($C_{1-6}$)alkyl or di($C_{1-6}$)alkylamino($C_{1-6}$)alkyl.

Suitably, $R^4$ represents hydrogen or methyl.

Suitably, $R^5$ represents hydrogen, methyl, ethyl, hydroxyethyl or dimethylaminoethyl. Particular values of $R^5$ include hydrogen, hydroxyethyl and dimethylaminoethyl.

Where $R^{11}$ represents heteroaryl, this group is suitably furyl.

Representative values of $R^{11}$ include methyl, hydroxymethyl, hydroxyethyl, furyl, chloro, fluoromethyl, difluoromethyl, trifluoromethyl, methoxy, formyl, acetyl, methoxycarbonyl and —$CR^2$=$NOR^3$, in which $R^2$ and $R^3$ are as defined above. Additionally, $R^{11}$ may represent hydroxypropyl.

Particular values of $R^{11}$ include methyl, fluoromethyl, difluoromethyl, trifluoromethyl and hydroxymethyl. In one embodiment, $R^{11}$ represents methyl. In another embodiment, $R^{11}$ represents trifluoromethyl.

A representative subset of the compounds of formula IIA above is represented by the compounds of formula IIB, and salts and prodrugs thereof:

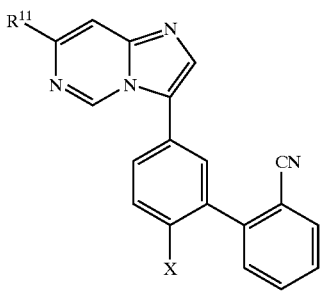

(IIB)

wherein X and R[11] are as defined above.

Specific compounds within the scope of the present invention include:

3'-(7-methylimidazo[1,2-c]pyrimidin-3-yl)biphenyl-2-carbonitrile;

2'-fluoro-5'-(7-trifluoromethylimidazo[1,2-c]pyrimidin-3-yl)biphenyl-2-carbonitrile;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 50 nM or less, preferably 10 nM or less, and more preferably 5 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk-fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

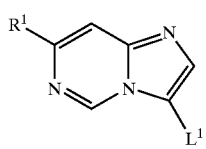

(III)

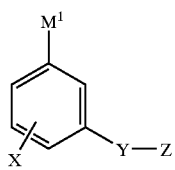

(IV)

wherein X, Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. bromo.

The transition metal catalyst of use in the reaction between compounds III and IV is suitably tetrakis (triphenylphosphine)-palladium(0). The reaction is conveniently carried out at an elevated temperature in a solvent such as N,N-dimethylacetamide, advantageously in the presence of potassium phosphate.

In an alternative procedure, the compounds according to the present invention in which Y represents a chemical bond may be prepared by a process which comprises reacting a compound of formula V with a compound of formula VI:

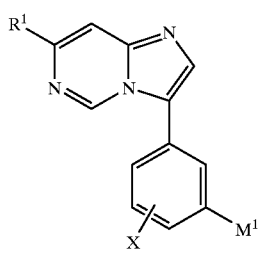

(V)

wherein X, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents an oxygen atom may be prepared by a process which comprises reacting a compound of formula VI as defined above with a compound of formula VII:

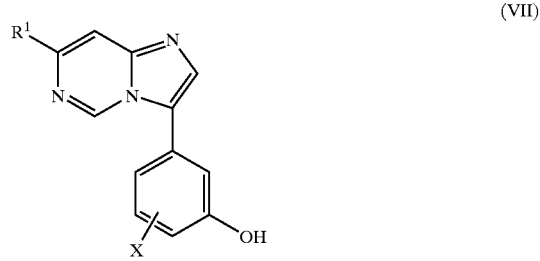

(VII)

wherein X and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula VI as defined above with a compound of formula VIII:

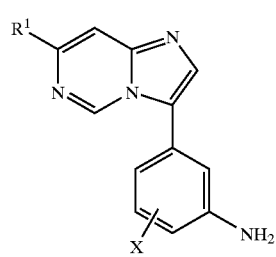

(VIII)

wherein X and $R^1$ are as defined above.

In relation to the reaction between compounds VI and VIII, the leaving group $L^1$ in the compounds of formula VI may suitably represent fluoro.

The reaction between compounds VI and VIII is conveniently carried out by heating the reactants, typically at a temperature in the region of 120° C., in a solvent such as N,N-dimethylformamide.

Where $M^1$ in the intermediates of formula IV and V above represents a cyclic ester of a boronic acid moiety —$B(OH)_2$ formed with pinacol, the relevant compound IV or V may be prepared by reacting bis(pinacolato)diboron with a compound of formula IVA or VA:

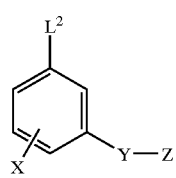

(IVA)

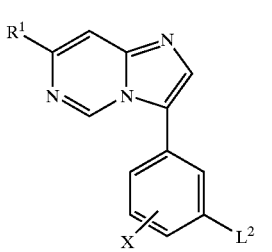

(VA)

wherein X, Y, Z and R¹ are as defined above, and L² represents hydroxy or a suitable leaving group; in the presence of a transition metal catalyst.

Where L² represents a leaving group, this is typically trifluoromethanesulfonyloxy (triflyloxy) or bromo.

The transition metal catalyst of use in the reaction between bis(pinacolato)diboron and compound IVA or VA is suitably dichloro[1,1'-bis(diphenylphosphino)ferrocene] palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where L² in the intermediates of formula VA above represents triflyloxy, the relevant compound VA may be prepared by reacting the appropriate compound of formula VII as defined above with triflic anhydride, typically in the presence of pyridine. Analogous conditions may be utilised for converting an intermediate of formula IVA above wherein L² represents hydroxy into the corresponding compound wherein L² represents triflyloxy.

The intermediates of formula VII above may suitably be prepared from the appropriate methoxy-substituted precursor of formula IX:

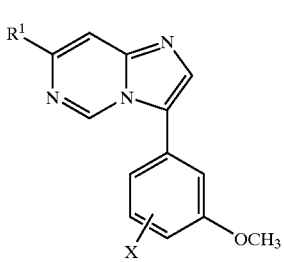

(IX)

wherein X and R¹ are as defined above; by treatment with hydrogen bromide, typically in acetic acid at reflux.

The intermediates of formula VIII and IX above may be prepared by reacting a compound of formula III as defined above with the appropriate compound of formula X:

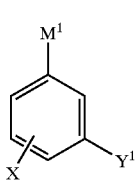

(X)

wherein X and M¹ are as defined above, and Y¹ represents amino or methoxy; in the presence of a transition metal catalyst; under conditions analogous to those described above for the reaction between compounds III and IV.

Where L¹ in the intermediates of formula III above represents bromo, this compound may be prepared by bromination of the corresponding compound of formula XI:

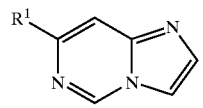

(XI)

wherein R¹ is as defined above; typically by treatment with bromine in acetic acid, in the presence of sodium acetate and optionally also potassium bromide.

The intermediates of formula XI may be prepared by reacting chloroacetaldehyde or bromoacetaldehyde with the requisite compound of formula XII:

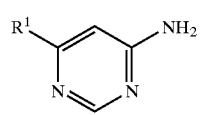

(XII)

wherein R¹ is as defined above.

The reaction is conveniently carried out by heating the reactants in a suitable solvent, e.g. a lower alkanol such as methanol and/or ethanol, or ethylene glycol dimethyl ether, at 60–80° C.

In a still further procedure, the compounds according to the present invention may be prepared by a process which comprises reacting a compound of formula XII as defined above with a compound of formula XIII:

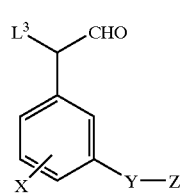

(XIII)

wherein X, Y and Z are as defined above, and L³ represents a suitable leaving group; under conditions analogous to those described above for the reaction between chloroacetaldehyde or bromoacetaldehyde and compound XII.

The leaving group L³ is suitably a halogen atom, e.g. bromo.

In a yet further procedure, the compounds according to the present invention wherein R¹ represents an aryl or heteroaryl moiety and X represents hydrogen may be prepared by a process which comprises reacting a compound of formula XIV with a compound of formula XV:

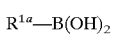

R¹ᵃ—B(OH)₂     (XIV)

(XV)

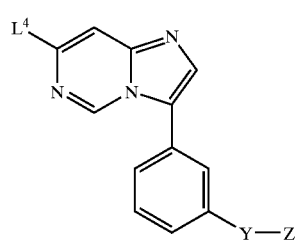

wherein Y and Z are as defined above, R¹ᵃ represents an aryl or heteroaryl moiety, and L⁴ represents a suitable leaving group; in the presence of a transition metal catalyst.

The leaving group $L^4$ is typically a halogen atom, e.g. chloro.

The transition metal catalyst of use in the reaction between compounds XIV and XV is suitably tris (dibenzylideneacetone)-dipalladium(0), in which case the reaction is conveniently effected at an elevated temperature in a solvent such as 1,4-dioxane, typically in the presence of tri-tert-butylphosphine and cesium carbonate.

Where $L^4$ in the compounds of formula XV above represents a halogen atom, these compounds correspond to compounds of formula I as defined above wherein $R^1$ represents halogen, and they may therefore be prepared by any of the methods described above for the preparation of the compounds according to the invention.

Where they are not commercially available, the starting materials of formula IV, VI, X, XII, XIII and XIV may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein $R^1$ represents $C_{1-6}$ alkoxycarbonyl initially obtained may be reduced with lithium aluminium hydride to the corresponding compound of formula I wherein $R^1$ represents hydroxymethyl. The latter compound may then be oxidised to the corresponding compound of formula I wherein $R^1$ represents formyl by treatment with manganese dioxide. The formyl derivative thereby obtained may be condensed with a hydroxylamine derivative of formula $H_2N$—$OR^b$ to provide a compound of formula I wherein $R^1$ represents —CH=$NOR^b$. Alternatively, the compound of formula I wherein $R^1$ represents formyl may be reacted with a Grignard reagent of formula $R^a MgBr$ to afford a compound of formula I wherein $R^1$ represents —CH(OH)$R^a$, and this compound may in turn be oxidised using manganese dioxide to the corresponding compound of formula I wherein $R^1$ represents —$COR^a$. The latter compound may then be condensed with a hydroxylamine derivative of formula $H_2N$—$OR^b$ to provide a compound of formula I wherein $R^1$ represents —$CR^a$=$NOR^b$.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk-cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

3'-(7-Methylimidazo[1,2-c]pyrimidin-3-yl)biphenyl-2-carbonitrile a) 4-Amino-6-methylpyrimidine To a stirred suspension of Raney® nickel (16.30 g) in water (30 ml) and 25% aqueous ammonia (60 ml) at 80° C. was added, portionwise over 15 min 4-amino-2-mercapto-6-methylpyrimidine (10.01 g, 70.9 mmol). The mixture was then heated at reflux for 23 h. The Raney® nickel was removed by filtration and washed well with water. The combined filtrates were evaporated in vacuo and purified by flash chromatography (silica gel, $CH_2Cl_2$—MeOH—$NH_3$ (aq); 90:10:1) to leave 5.25 g (68%) of the title compound as a whitish solid: $^1$H NMR (360 MHz, DMSO-d$_6$) δ 2.17 (3H, s), 6.24 (1H, s), 6.64 (2H, br s), 8.21 (1H, s).

b) 7-Methylimidazo[1,2-c]pyrimidine

A stirred mixture of bromoacetaldehyde diethyl acetal (3.43 ml, 22.1 mmol) in concentrated hydrobromic acid (1.1 ml) and water (1.1 ml) was heated at reflux under nitrogen for 2 h, then poured into ethanol (57 ml). The solution was neutralised to pH 7 with solid sodium hydrogen carbonate, then filtered. To the filtrate was added 4-amino-6-methylpyrimidine (1.0063 g, 9.22 mmol) and the mixture was stirred at room temperature for 30 min then at 60° C. for 19 h. After allowing to cool, the solvent was removed in vacuo and the residue was purified by flash chromatography (silica gel, 5–10% MeOH/CH$_2$CO$_2$) to give 0.5071 g (41%) of the title compound: $^1$H NMR (360 MHz, CDCl$_3$) δ 2.54 (3H, s), 7.33 (1H, s), 7.59 (1H, s), 7.62 (1H, d, J 1.2 Hz), 8.96 (1H, s); MS (ES$^+$) m/z 134 [M+H]$^+$.

c) 3-Bromo-7-methylimidazo[1,2-c]pyrimidine

To a solution of 7-methylimidazo[1,2-c]pyrimidine (0.3404 g, 2.56 mmol) in acetic acid (10 ml) was added sodium acetate (0.3132 g, 3.82 mmol), then, dropwise over 7 min, a solution of bromine (66.0 μl, 1.28 mmol) in acetic acid (2 ml). The solution was stirred at room temperature for 20 min, then more bromine (19.7 μl, 0.382 mmol) in acetic acid (0.6 ml) was added over 4 min. The solution was stirred at room temperature for a further 15 min, then partitioned between saturated aqueous NaHCO$_3$ (200 ml) and ethyl acetate (200 ml). The aqueous layer (pH 9) was further extracted with ethyl acetate (200 ml), and the combined organic extracts were dried (Na$_2$SO$_4$) and evaporated in vacuo. The residue was purified by flash chromatography (silica gel, EtOAc) to afford 0.2298 g (42%) of the title compound: $^1$H NMR (360 MHz, CDCl$_3$) δ 2.57 (3H, s), 7.29 (1H, s), 7.56 (1H, s), 8.91 (1H, s); MS (ES$^+$) m/z 212/214 [M+H]$^+$.

d) 3'-(7-Methylimidazo[1,2-c]pyrimidin-3-yl)biphenyl-2-carbonitrile

A mixture of 2-bromobenzonitrile (9.1 g, 50 mmol), 3-aminobenzeneboronic acid monohydrate (11.6 g, 75 mmol) and tetrakis(triphenylphosphine)palladium(0) (1.73 g, 1.5 mmol) in 1,2-dimethoxyethane (50 ml) and 2 M aqueous sodium carbonate (25 ml) was heated at 80° C. for 20 h. After cooling to ambient temperature the reaction was partitioned between ethyl acetate (400 ml) and water (400 ml). The organic layer was washed with brine (400 ml), dried (Na$_2$SO$_4$), and evaporated in vacuo. Purification of the residue by flash chromatography (silica gel, 0–25% EtOAc/ isohexane) gave 9.5 g (98%) of 3'-aminobiphenyl-2-carbonitrile as a colourless oil that solidified on standing to afford a white solid: $^1$H NMR (400 MHz, CDCl$_3$) δ 3.79 (2H, br), 6.75 (1H, ddd, J 8, 3, 1 Hz), 6.84 (1H, dd, J 3, 3 Hz), 6.92 (1H, dd, J 8, 3 Hz), 7.25 (1H, dd, J 8, 8 Hz), 7.40 (1H, ddd, J 8, 8, 1 Hz), 7.50 (1H, dd, J 8, 1 Hz), 7.62 (1H, ddd, J 8, 8, 1 Hz), 7.73 (1H, dd, J 8, 1 Hz).

A solution of 3'-aminobiphenyl-2-carbonitrile (10.9 g, 56 mmol) in 1,4-dioxane (30 ml) was treated with a solution of 25% aqueous sulfuric acid (150 ml). The resulting suspension was cooled to 0° C. before being treated dropwise over 10 minutes with a solution of sodium nitrite (4.6 g, 67 mmol) in water (10 ml). After stirring at 0° C. for 30 minutes the reaction was poured into hot (70° C.) water (500 ml). On cooling to ambient temperature the product was extracted into ethyl acetate (500 ml), the organic layer was washed with water (300 ml), brine (300 ml) and dried (Na$_2$SO$_4$). Filtration and concentration in vacuo afforded 7.1 g (65%) of 3'-hydroxybiphenyl-2-carbonitrile as a dark oil: $^1$H NMR (400 MHz, CDCl$_3$) δ 5.40 (1H, br), 6.92 (1H, ddd, J 8, 3, 1 Hz), 7.04 (1H, dd, J 3, 3 Hz), 7.11 (1H, ddd, J 8, 3, 1 Hz), 7.35 (1H, dd, J 8, 8 Hz), 7.44 (1H, ddd, J 8, 8, 1 Hz), 7.51 (1H, dd, J 8, 1 Hz), 7.64 (1H, ddd, J 8, 8, 1 Hz), 7.75 (1H, dd, J 8, 1 Hz).

3'-Hydroxybiphenyl-2-carbonitrile (0.48 g, 2.47 mmol) and dry pyridine (0.98 g, 12.35 mmol) were dissolved in dichloromethane (7 ml) and cooled to 0° C. before the dropwise addition of trifluoromethanesulfonic anhydride (1.04 g, 3.70 mmol) over 5 min. The mixture was stirred at 0° C. for 10 min and then at 25° C. for 1 h. The solvent was evaporated in vacuo and the residue was partitioned between ethyl acetate (200 ml) and water (150 ml). The organic layer was washed with brine (150 ml), dried (Na$_2$SO$_4$) and evaporated in vacuo to give a brown oil. Purification by chromatography (silica gel, 0–30% EtOAc/isohexane) gave 544 mg (67%) of trifluoromethanesulfonic acid 2'-cyanobiphenyl-3-yl ester as a yellow oil: $^1$H NMR (400 MHz, CDCl$_3$) δ 7.37 (1H, ddd, J 8, 3, 1 Hz), 7.39 (1H, dd, J 3, 3 Hz), 7.50–7.60 (2H, m), 7.61–7.65 (2H, m), 7.64 (1H, td, J 8, 1 Hz), 7.80 (1H, dd, J 8, 1 Hz).

Trifluoromethanesulfonic acid 2'-cyanobiphenyl-3-yl ester (0.55 g, 1.66 mmol), potassium acetate (0.49 g, 4.98 mmol) and bis(pinacolato)diboron (0.55 g, 2.16 mmol) were dissolved in 1,4-dioxane (10 ml) and the mixture degassed with nitrogen for 15 min. Dichloro[1,1'-bis(diphenylphosphino)ferrocene]palladium(II) dichloromethane adduct (41 mg, 0.05 mmol) and 1,1'-bis(diphenylphosphino)ferrocene (28 mg, 0.05 mmol) were then added and the mixture heated at 85° C. for 18 h. The mixture was cooled to ambient temperature and partitioned between ethyl acetate (150 ml) and water (50 ml). The organic layer was washed with brine (50 ml), dried (Na$_2$SO$_4$), and evaporated in vacuo to give 0.51 g (100%) of 3'-(4,4,5,5-tetramethyl-[1,3,2]dioxaborolan-2-yl)biphenyl-2-carbonitrile as a black oil. This oil was dissolved in sufficient N,N-dimethylacetamide to give a 0.5 M stock solution.

A stirred mixture of 3-bromo-7-methylimidazo[1,2-c]pyrimidine (0.1013 g, 0.478 mmol), dried potassium phosphate (0.2027 g, 0.955 mmol) and a 0.5 M solution of 3'-(4,4,5,5-tetramethyl-[1,3,2]dioxaborolan-2-yl)-biphenyl-2-carbonitrile in N,N-dimethylacetamide (1.91 ml, 0.955 mmol) was degassed by evacuation and refilling with nitrogen three times. Tetrakis(triphenylphosphine)palladium(0) (28.7 mg, 0.0248 mmol) was then added and the mixture was degassed with two more evacuation-refilling cycles before heating at 80° C. under nitrogen for 45 h, adding more dried potassium phosphate (0.0503 g, 0.237 mmol), a 0.5 M solution of 3'-(4,4,5,5-tetramethyl-[1,3,2] dioxaborolan-2-yl)biphenyl-2-carbonitrile in N,N-dimethylacetamide (0.48 ml, 0.240 mmol) and tetrakis (triphenylphosphine)palladium(0) (8.0 mg, 0.0069 mmol) after 21 h with degassing. The mixture was diluted with ethyl acetate and filtered through glass fibre filter paper, washing solid with more ethyl acetate. The combined filtrates were washed with saturated aqueous NaCl (15 ml), and the aqueous layer was further extracted with ethyl acetate (2×25 ml). The combined organic extracts were dried (Na$_2$SO$_4$) and evaporated in vacuo. The residue was purified by flash chromatography (silica gel, EtOAc) to give 72.8 mg (49%) of the title compound as a yellow-brown solid: mp 119° C. (softens) (CH$_2$Cl$_2$-EtOAc-isohexane); $^1$H NMR (400 MHz, CDCl$_3$) δ 2.57 (3H, s), 7.36 (1H, s), 7.51 (1H, td, J 7.6, 1.2 Hz), 7.57–7.72 (6H, m), 7.78 (1H, fine m), 7.82 (1H, dd, J 7.5, 1.4 Hz), 9.34 (1H, s); MS (ES$^+$) m/z 311 [M+H]$^+$; Anal. Found: C, 71.93; H, 4.68; N, 16.35%. Required for C$_{20}$H$_{14}$N$_4$·1.4H$_2$O: C, 71.58; H, 5.05; N, 16.70.

EXAMPLE 2

2'-Fluoro-5'-(7-trifluoromethylimidazo[1,2-c]pyrimidin-3-yl)biphenyl-2-carbonitrile a) 4-Amino-6-trifluoromethylpyrimidine To a stirred mixture of 4-chloro-6-trifluoromethylpyrimidine (prepared from 6-trifluoromethyl-4-pyrimidinol as described in U.S. Pat. No. 5,714,438) (17.14 g, 93.9 mmol) in acetonitrile (282 ml) was added 25% aqueous ammonia solution (564 ml) and the mixture was stirred at room temperature for 23 h. The mixture was extracted with ethyl acetate (3×1 l), and the combined extracts were dried (MgSO$_4$) and evaporated in vacuo to leave 14.97 g (98%) of the title compound as a white solid: $^1$H NMR (360 MHz, DMSO-d$_6$) δ 6.80 (1H, s), 7.52 (2H, br s), 8.49 (1H, s).

b) 3-Bromo-7-trifluoromethylimidazo[1,2-c]pyrimidine

A stirred mixture of bromoacetaldehyde diethyl acetal (2.09 ml, 13.5 mmol) in concentrated hydrobromic acid (0.68 ml) and water (0.68 ml) was heated at reflux under nitrogen for 20 min. The solution was allowed to cool to room temperature, ethylene glycol dimethyl ether (5 ml) was added and the solution was neutralised to pH 7 with solid sodium hydrogen carbonate. The mixture was filtered and the solid was washed with more ethylene glycol dimethyl ether (7 ml). To the combined filtrates was added 4-amino-6-trifluoromethylpyrimidine (2.00 g, 12.3 mmol) and the mixture was stirred at 65° C. for 18 h. After allowing to cool, the solvent was removed in vacuo and the residue was purified by flash chromatography (silica gel, 5% MeOH/CH$_2$Cl$_2$) to give 2.426 g of 7-trifluoromethylimidazo[1,2-c]pyrimidine: $^1$H NMR (360 MHz, CDCl$_3$) δ 7.81 (1H, s), 7.86 (1H, s), 7.96 (1H, s), 9.13 (1H, s).

To a solution of 7-trifluoromethylimidazo[1,2-c]pyrimidine (1.9239 g, 10.3 mmol) in acetic acid (40 ml) was added sodium acetate (1.265 g, 15.4 mmol), then a solution of bromine (0.529 ml, 10.3 mmol) in acetic acid (7.5 ml). The solution was stirred at room temperature for 30 min, then partitioned between saturated aqueous NaHCO$_3$ (1 l) and ethyl acetate (500 ml). The aqueous layer (pH 8) was further extracted with ethyl acetate (500 ml), and the combined organic extracts were dried (Na$_2$SO$_4$) and evaporated in vacuo. The residue was purified by flash chromatography (silica gel, 20% EtOAc/isohexane) to afford 0.88 g (34% over 2 steps) of the title compound as a white solid: $^1$H NMR (360 MHz, CDCl$_3$) δ 7.81 (1H, s), 7.93 (1H, s), 9.09 (1H, s).

c) 2'-Fluoro-5'-(7-trifluoromethylimidazo[1,2-c]pyrimidin-3-yl)biphenyl-2-carbonitrile A mixture of 3-bromo-4-fluoro-1-nitrobenzene (A. Groweiss, *Org. Process Res. Dev.*, 2000, 4, 30–33) (50.10 g, 0.228 mol), dried potassium acetate (44.70 g, 0.455 mol) and bis(pinacolato)diboron (59.16 g, 0.233 mol) in 1,4-dioxane (539 ml) and dimethylsulfoxide (11 ml) was degassed by bubbling nitrogen through the mixture for 1 h. Dichloro[1,1'-bis(diphenylphosphino)ferrocene]palladium(II) dichloromethane adduct (5.58 g, 6.83 mmol) was added and the mixture was stirred at 90° C. under nitrogen for 18.5 h, adding more bis(pinacolato)diboron (7.34 g, 0.029 mol) after 2.5 h. After allowing to cool, the mixture was filtered through glass fibre paper, and the solid was washed with a little dichloromethane. The combined filtrates were evaporated in vacuo and the residue was partitioned between 2 M aqueous NaOH (800 ml) and diethyl ether (800 ml). The aqueous layer was then acidified to pH 6 with concentrated hydrochloric acid (120 ml), causing a solid to precipitate. After leaving in a fridge for 3 days, the solid was collected by filtration, washed with water and dried under vacuum to leave 54.82 g (90%) of 2-fluoro-5-nitrobenzeneboronic acid pinacol cyclic ester: $^1$H NMR (360 MHz, DMSO-d$_6$) δ 1.33 (12H, s), 7.48 (1H, m), 8.40–8.45 (2H, m).

A mixture of 2-fluoro-5-nitrobenzeneboronic acid pinacol cyclic ester (37.62 g, 0.141 mol), 2-bromobenzonitrile (35.30 g, 0.194 mol) and tetrakis(triphenylphosphine)palladium(0) (5.85 g, 5.06 mmol) in ethylene glycol dimethyl ether (350 ml) and saturated aqueous NaHCO$_3$ (150 ml) was degassed by bubbling nitrogen through the mixture for 30 min. The mixture was then stirred at 90° C. under nitrogen for 15 h. After allowing to cool, the mixture was partitioned between dichloromethane (500 ml) and water (400 ml). The organic layer was washed with brine, dried (MgSO$_4$), then passed through a pad of Florisil®, washing the product through with more dichloromethane. The filtrates were evaporated in vacuo, and the residue was triturated with diethyl ether (100 ml) and isohexane (100 ml). The resulting solid was collected by filtration, washed with 50% Et$_2$O/isohexane and dried under vacuum to give 14.82 g (43%) of 2'-fluoro-5'-nitrobiphenyl-2-carbonitrile as a white solid. The combined filtrates were concentrated in vacuo to approximately 100 ml and the resulting solid was collected by filtration, washed with 20% Et$_2$O/isohexane and dried under vacuum to give another 0.94 g (3%) of the product. The filtrates were evaporated in vacuo, and the residue was purified by flash chromatography (silica gel, 10–15% EtOAc/isohexane) to afford another 3.07 g (9%) of the product: $^1$H NMR (360 MHz, CDCl$_3$) δ 7.40 (1H, t, J 8.5 Hz), 7.53 (1H, d, J 7.8 Hz), 7.59 (1H, td, J 7.7, 1.1 Hz), 7.74 (1H, td, J 7.7, 1.3 Hz), 7.84 (1H, dd, J 7.7, 0.9 Hz), 8.34–8.39 (2H, m).

To a stirred suspension of 2'-fluoro-5'-nitrobiphenyl-2-carbonitrile (18.71 g, 77.2 mmol) in THF (150 ml) and ethanol (150 ml) was added tin(II) chloride dihydrate (52.42 g, 232.4 mmol) and the mixture was stirred at room temperature for 22.5 h. The mixture was evaporated in vacuo and the residue was treated with ice-cold 2 N aqueous NaOH (800 ml). The resulting mixture was stirred for 1.5 h, then extracted with dichloromethane (2×800 ml). The combined organic extracts were washed with saturated aqueous NaCl (200 ml), dried (MgSO$_4$), and evaporated in vacuo. The residue was recrystallised from hot toluene (100 ml) to afford 11.33 g (69%) of 5'-amino-2'-fluorobiphenyl-2-carbonitrile as a white solid: $^1$H NMR (360 MHz, CDCl$_3$) δ 3.65 (2H, br s), 6.67–6.73 (2H, m), 7.00 (1H, t, J 9.0 Hz), 7.46 (1H, td, J 7.6, 1.1 Hz), 7.49 (1H, d, J 7.4 Hz), 7.64 (1H, td, J 7.7, 1.3 Hz), 7.76 (1H, dd, J 7.7, 0.7 Hz).

To a solution of 5'-amino-2'-fluorobiphenyl-2-carbonitrile (11.17 g, 52.6 mmol) in 1,4-dioxane (60 ml) was added 48% hydrobromic acid (250 ml) and the resulting suspension was cooled to 2° C., whilst stirring with an air stirrer. To this was added, dropwise over 20 min, a solution of sodium nitrite (4.18 g, 60.6 mmol) in water (11 ml), keeping the temperature below 5° C. The mixture was then stirred at 2±2° C. for 2 h before adding a cooled (5° C.) solution of freshly purified copper(I) bromide (25.40 g, 177.1 mmol) in 48% hydrobromic acid (75 ml). The mixture was stirred at 1±1° C. for 10 min before heating to 47° C. over 1 h. The mixture was diluted with ice-cold water (1.25 l) and extracted with ethyl acetate (2×500 ml). The combined organic extracts were washed with 1 M aqueous Na$_2$SO$_3$ (100 ml), then saturated aqueous NaCl (100 ml), dried (MgSO$_4$) and evaporated in vacuo to leave 16.08 g of 5'-bromo-2'-fluorobiphenyl-2-carbonitrile as a light brown solid: $^1$H NMR (360 MHz, CDCl$_3$) δ 7.12 (1H, t, J 9.1 Hz), 7.47–7.57 (4H, m), 7.68 (1H, td, J 7.7, 1.3 Hz), 7.79 (1H, d, J 7.8 Hz).

A mixture of the crude 5'-bromo-2'-fluorobiphenyl-2-carbonitrile (16.08 g), dried potassium acetate (10.33 g, 0.105 mol) and bis(pinacolato)diboron (15.37 g, 60.5 mmol) in 1,4-dioxane (123 ml) and dimethylsulfoxide (2.5 ml) was degassed by bubbling nitrogen through the mixture for 1 h. Dichloro[1,1'-bis(diphenylphosphino)ferrocene]-palladium (II) dichloromethane adduct (1.29 g, 1.58 mmol) was added and the mixture was stirred at 90° C. under nitrogen for 15.5 h. After allowing to cool, the mixture was filtered through glass fibre paper, and the solid was washed with a little dichloromethane. The combined filtrates were evaporated in vacuo and the residue was partitioned between 2 M aqueous NaOH (200 ml) and diethyl ether (200 ml). The aqueous layer was washed with more diethyl ether (100 ml), then acidified to pH 6 with concentrated hydrochloric acid (35 ml), causing a solid to precipitate. After leaving in a fridge for 3 days, the solid was collected by filtration, washed with water and dried under vacuum to leave 13.37 g (79% over two steps) of 2'-fluoro-5'-(4,4,5,5-tetramethyl-[1,3,2] dioxaborolan-2-yl)biphenyl-2-carbonitrile: $^1$H NMR (360 MHz, CDCl$_3$) δ 1.35 (12H, s), 7.21 (1H, t, J 9.3 Hz), 7.45–7.51 (2H, m), 7.65 (1H, t, J 7.7 Hz), 7.76 (1H, d, J 7.6 Hz), 7.83 (1H, d, J 7.8 Hz), 7.88 (1H, m).

A stirred mixture of 3-bromo-7-trifluoromethylimidazo[1,2-c]pyrimidine (100 mg, 0.375 mmol), dried potassium phosphate (0.159 g, 0.750 mmol) and 2'-fluoro-5'-(4,4,5,5-tetramethyl-[1,3,2]dioxaborolan-2-yl)biphenyl-2-carbonitrile (0.2424 g, 0.750 mmol) in anhydrous N,N-dimethylacetamide (2 ml) was degassed by evacuation and refilling with nitrogen three times. Tetrakis (triphenylphosphine)palladium(0) (22 mg, 0.019 mmol) was then added and the mixture was degassed with two more evacuation-refilling cycles before heating at 80° C. under nitrogen for 3 h. The mixture was partitioned between ethyl acetate (250 ml) and brine (250 ml), and the aqueous layer was extracted further with ethyl acetate (250 ml). The combined organic extracts were dried (Na$_2$SO$_4$) and evaporated in vacuo. The residue was purified by flash chromatography (silica gel, 40% EtOAc/isohexane), then recrystallisation (EtOAc) to give 6.8 mg (5%) of the title compound: $^1$H NMR (400 MHz, CDCl$_3$) δ 7.46 (1H, t, J 8.6 Hz), 7.56 (1H, td, J 7.7, 1.3 Hz), 7.60 (1H, m), 7.65-7.74 (3H, m), 7.85 (1H, dd, J 7.8, 1.6 Hz), 7.89 (1H, s), 7.99 (1H, s), 9.37 (1H, s); MS (ES$^+$) m/z 383 [M+H]$^+$.

What is claimed is:

1. A compound of formula I, or a salt thereof:

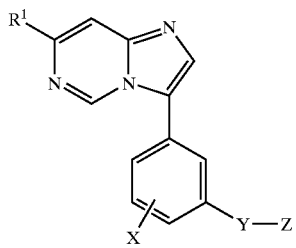

(I)

wherein:
  X represents hydrogen or halogen;
  Y represents a chemical bond, an oxygen atom, or a —NH— linkage;
  Z represents an aryl or heteroaryl group, which is unsubstituted or substituted with a substituent selected from halogen, cyano, nitro, amino, formyl, $C_{2-6}$ alkoxycarbonyl, —CR$^a$=NOR$^b$, trifluoromethyl, $C_{1-6}$ alkoxy and —CONR$^a$R$^b$;
  R$^1$ represents hydrogen, hydrocarbon, a heterocyclic group, halogen, cyano, trifluoromethyl nitro, —OR$^a$,
—SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$ or —CR$^a$=NOR$^b$; and
  R$^a$ and R$^b$ independently represent hydrogen, hydrocarbon or a heterocyclic group.

2. The compound of claim 1 of the formula IIA, or a salt thereof:

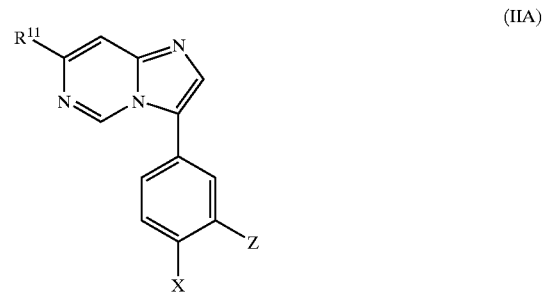

(IIA)

wherein
  R$^{11}$ represents $C_{1-6}$ alkyl, halo($C_{1-6}$)alkyl, dihalo($C_{1-6}$) alkyl, hydroxy($C_{1-6}$)alkyl, heteroaryl, halogen, trifluoromethyl, $C_{1-6}$ alkoxy, formyl, $C_{2-6}$ alkylcarbonyl, $C_{2-6}$ alkoxycarbonyl or —CR$^4$=NOR$^5$;
  R$^4$ represents hydrogen or $C_{1-6}$ alkyl; and
  R$^5$ represents hydrogen, $C_{1-6}$ alkyl, hydroxy($C_{1-6}$)alkyl or di($C_{1-6}$)alkylamino($C_{1-6}$)alkyl.

3. The compound of claim 2 of the formula IIB, or a salt thereof:

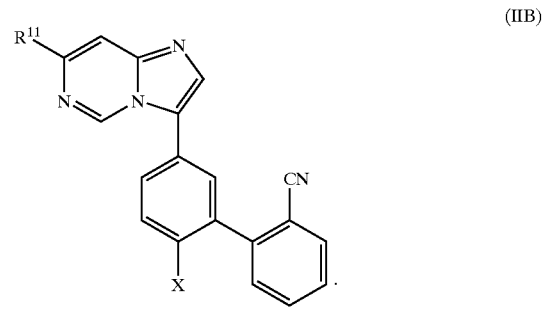

(IIB)

4. A compound which is selected from:
  3'-(7-methylimidazo[1,2-c]pyrimidin-3-yl)biphenyl-2-carbonitrile;
  2'fluoro-5'-(7-trifluoromethylimidazo[1,2-c]pyrimidin-3-yl)biphenyl-2-carbonitrile;
or a salt thereof.

5. A pharmaceutical composition comprising the compound of claim 1 or a pharmaceutically acceptable salt thereof and a pharmaceutically acceptable carrier.

6. A method for the treatment of anxiety which comprises administering to a patient in need of such treatment an effective amount of the compound of claim 1 or a pharmaceutically acceptable salt thereof.

7. A method for the treatment of convulsions which comprises administering to a patient in need of such treatment an effective amount of the compound of claim 1 or a pharmaceutically acceptable salt thereof.

8. A process for the preparation of the compound of claim 1, which comprises:

(A) reacting a compound of formula III with a compound of formula IV:

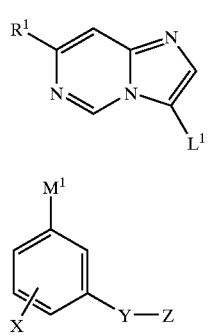

(III)

(IV)

wherein X, Y, and $R^1$ are as defined in claim 1, $L^1$ represents a suitable leaving group, and $M^1$ represents a boronic acid moiety —B(OH)2 or a cyclic ester thereof formed with an organic diol, or $M^1$ represents —Sn(Alk)$_3$ in which Alk represents $C_{1-6}$ alkyl; in the presence of a transition metal catalyst; or (B) reacting a compound of formula V with a compound of formula VI:

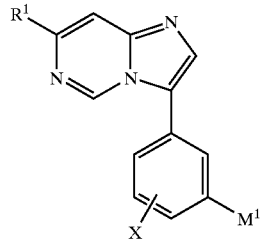

(V)

L$^1$-Z (VI)

wherein X, Z and $R^1$ are as defined in claim 1, and $L^1$ and $M^1$ are as defined above; in the presence of a transition metal catalyst; or (C) reacting a compound of formula VI as defined above with a compound of formula VII:

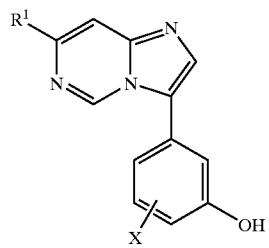

(VII)

wherein X and $R^1$ are as defined in claim 1; or (D) reacting a compound of formula VI as defined above with a compound of formula VIII:

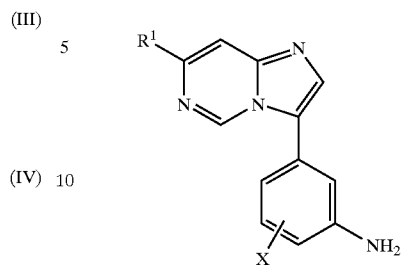

(VIII)

wherein X and $R^1$ are as defined in claim 1; or (E) reacting a compound of formula XII with a compound of formula XIII:

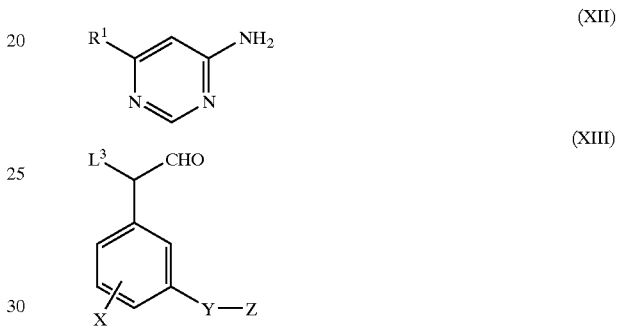

(XII)

(XIII)

wherein X, Y, Z and $R^1$ are as defined in claim 1, and $L^3$ represents a suitable leaving group; or (F) reacting a compound of formula XIV with a compound of formula XV:

$R^{1a}$—B(OH)$_2$ (XIV)

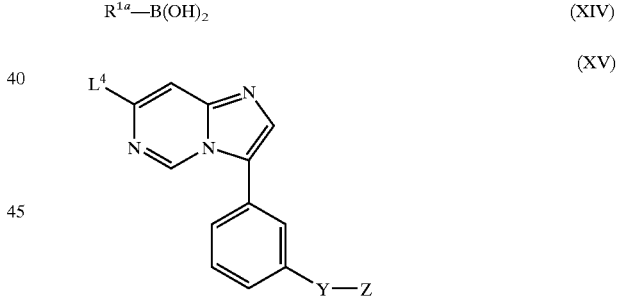

(XV)

wherein Y and Z are as defined in claim 1, $R^{1a}$ represents an aryl or heteroaryl moiety, and $L^4$ represents a suitable leaving group; in the presence of a transition metal catalyst; and (G) if desired, converting a compound of formula I initially obtained into a further compound of formula I by standard methods.

* * * * *